United States Patent [19]

Levin

[11] 4,031,623
[45] June 28, 1977

[54] LINGUAL BLADED TOOTH

[76] Inventor: Bernard Levin, 2077 E. Meadowbrook Road, Altadena, Calif. 91001

[22] Filed: June 23, 1975

[21] Appl. No.: 589,057

[52] U.S. Cl. .................................................. 32/8
[51] Int. Cl.² ...................................... A61C 13/00
[58] Field of Search ........................ 32/2, 8, 13, 12

[56] References Cited

UNITED STATES PATENTS

| 2,549,636 | 4/1951 | Raber | 32/8 |
| 2,593,815 | 4/1952 | Vidaver | 32/8 |
| 2,659,145 | 11/1953 | Gillman | 32/15 |

*Primary Examiner*—Robert Peshock
*Attorney, Agent, or Firm*—Marvin H. Kleinberg

[57] ABSTRACT

An anatomical artificial tooth, used for complete or partial dentures, is provided with a metal insert located on a lingual cusp of the tooth, the insert having a blade configuration on its occlusal surface for the efficient cutting, shearing and shredding of food.

11 Claims, 8 Drawing Figures

OCCLUSAL VIEW

BUCCAL VIEW

LINGUAL VIEW

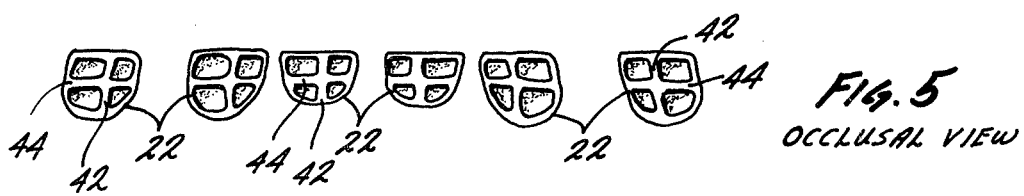
Fig. 5 OCCLUSAL VIEW
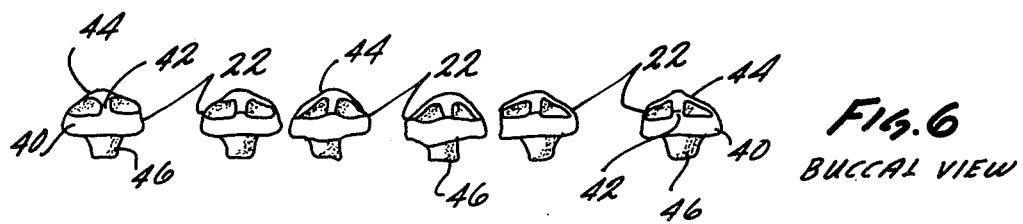
Fig. 6 BUCCAL VIEW
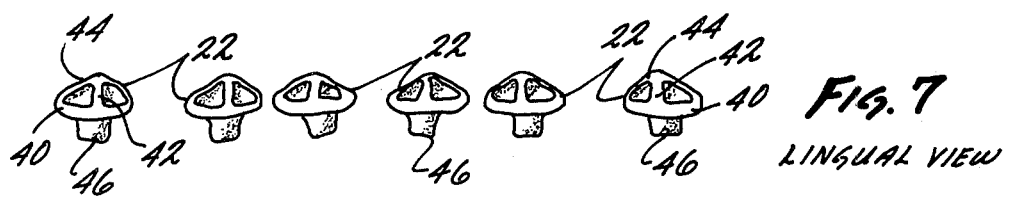
Fig. 7 LINGUAL VIEW
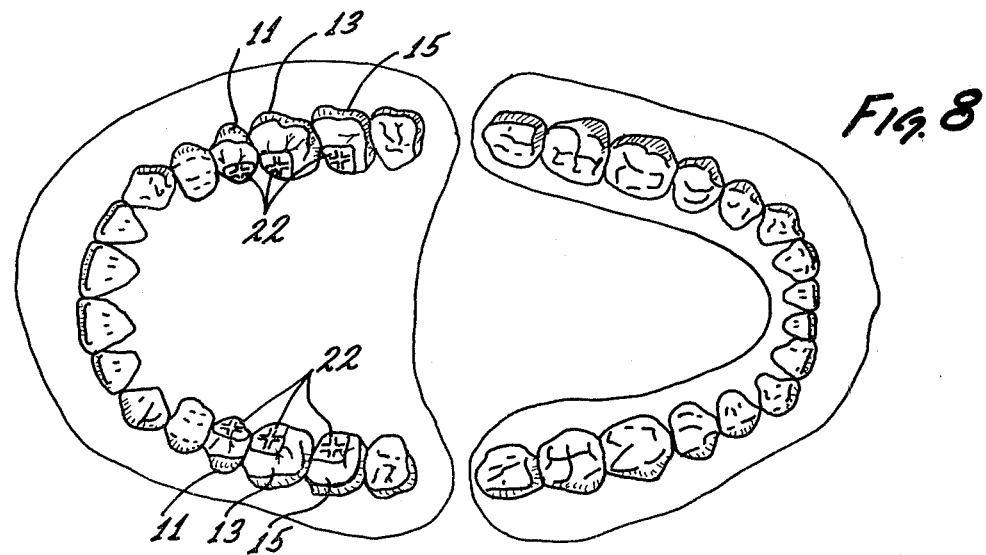
Fig. 8

LINGUAL BLADED TOOTH

BACKGROUND OF THE INVENTION

1. Field of the Invention

The present invention is in the field of prosthodontics and more specifically relates to an improved design for artificial teeth for use in complete and partial dentures.

2. Description of the Prior Art

With his natural teeth a man can exert over 100 pounds of chewing force comfortably. In the edentulous mouth the maximum pressure which can be exerted is on the average of only 15–20 pounds. For this reason, if artificial teeth are constructed in the same shape as the natural teeth, they will be grossly inadequate to perform the masticating function. Hence, anatomically formed teeth, while cosmetically correct, do not meet the functional requirements of artificial dentures. According to the studies of R. S. Manly ("Factors Affecting Masticatory Performance and Efficiency Among Young Adults", Journal of Dental Research, Vol. 30, p.p. 874–882, 1952) and K. Kapur and S. Soman, ("Masticatory Performance and Efficiency in Denture Wearers", Journal of Prosthetic Dentistry, Vol. 14, p.p. 687–694, 1964), the present denture teeth are about one sixth as efficient as natural teeth.

An article by I. R. Hardy in the Journal of Prosthetic Dentistry, Volume I, Nos. 1 and 2, page 14, January and March 1951, entitled "The Developments in the Occlusal Patterns of Artificial Teeth" surveyed the history of the development of nonanatomic teeth.

An early example of nonanatomic teeth were developed by F. A. French and described in "As We Progress; Why Modify Posterior Tooth Forms?" Dental Items of Interest, Vol. 57, pages 730–741, 1935. French wanted to use a Monoplane concept and he also wanted to improve the efficiency and stability. He designed a monoplane tooth (the early design had a slight cusp rise on the maxillary teeth but a later version is completely flat) by removing the mandibular buccal half of the tooth. He placed an elevated narrow ridge of porcelain mesiodistally on the center and linqual of the mandibular occlusal surface. Later, the teeth were re-designed with the ridge of porcelain only in the center. The porcelain ridges however proved to be friable.

In 1946, Hardy, as further described in the above article, developed a serpentine-shaped cutting blade of metal, which extended across the occlusal surfaces of several teeth. These teeth were good for shredding but the blades were not long enough to provide efficient cutting. Dentures made with this blade could not be balanced (a dental term which means even contact of all teeth when the patient moves his jaw to other positions) because the serpentine pattern was flat, whereas teeth need to have a curved occlusal surface. Furthermore, these teeth were definitely not esthetic.

In an article in the Journal of Prosthetic Dentistry, Vol. 11, No. 1, pages 55–61, January-February 1961 entitled "Re-evaluation of Posterior Tooth Forms for Complete Dentures", M. B. Sosin described a blade mechanism technique he had developed, in which the entire occlusal surfaces of the maxillary first and second molars and second bicuspids were replaced by six bladed structures cast in a cobalt-chromium-molybdenum alloy. The structures are 8 millimeters in diameter and 4 millimeters in height.

These blades on the upper denture occupied the entire occlusal surface of the tooth, and were opposed by metal tables on the lower denture occupying its entire occlusal surface. As Sosin comments (page 56) ". . . esthetics is not a serious consideration." The teeth were, however, extremely efficient and functional. The technique described is very difficult and is not within the capabilities of the average dentist.

Thus it is clear from the prior art that there is a need for an artificial tooth that combines the efficient masticating capability of the "bladed" tooth with the esthetically pleasing appearance of the "anatomical" tooth, and also a need for a tooth that can be used by the average dentist, both in balanced and non-balanced occlusion, as both concepts are accepted by the dental profession.

SUMMARY OF THE INVENTION

In the preferred embodiment of the present invention, an anatomical artificial tooth is provided with a metallic insert located on the lingual cusp of the tooth. The insert has a cross-blade configuration on its occlusal surface for efficient cutting, shearing, and shredding. These artificial teeth are normally mounted as second bicuspids, first and second molars in the upper denture at the rear of the dental arch, and normally are opposed by corresponding artificial anatomical or non-anatomical teeth of acrylic resin.

In one embodiment of the present invention, stainless steel blades in a cruciform configuration having edges conforming to the normal shape of the lingual cusp, are precast at the end of an integral post. Next, the precast post is mounted extending into a mold into which the acrylic resin is flowed to form the tooth. When the resin has cured, the precast metal insert is found to be securely anchored to the tooth at a position normally occupied by the lingual cusp of the tooth. The artificial teeth thus formed can be included in dentures in the usual manner.

The main advantage of the lingual cross-bladed tooth of the present invention is that the patient can eat better since the tooth permits more efficient mastication of the food. A further advantage of the present invention is that it places the more durable, malleable material at the point of greatest stress. This is important in the edentulous mouth where loss of peridontal tactile sense can result in excessive pressure being exerted against the tooth.

It has been found (by M. B. Sosin over a 20-year period) that the metallic blades retain their initial sharpness for years. If they should become dull, a dentist can easily "sharpen" them with ordinary instruments. Finally, because the metallic insert is only on the lingual cusp of a tooth, an esthetically pleasing, natural appearance is presented to the buccal side of the tooth. The casual observer is therefore unaware that the teeth are in any respect "different". Another major advantage is that these teeth may be used opposing any other type of resin denture teeth, 33°, 30°, 20°, 10°, or 0°. They can be set in balance or non-balance (balance in centric relation only) as the dentist prefers.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

BRIEF DESCRIPTION OF THE FIGURES

FIG. 5 is an occlusal view of the bladed insert according to the present invention;

FIG. 6 is a buccal view of the bladed insert;

FIG. 7 is a lingual view of the bladed insert; and

FIG. 8 is an occlusal view of upper and lower dentures according to the present invention.

DESCRIPTION OF THE PREFERRED EMBODIMENT

Figure 1:
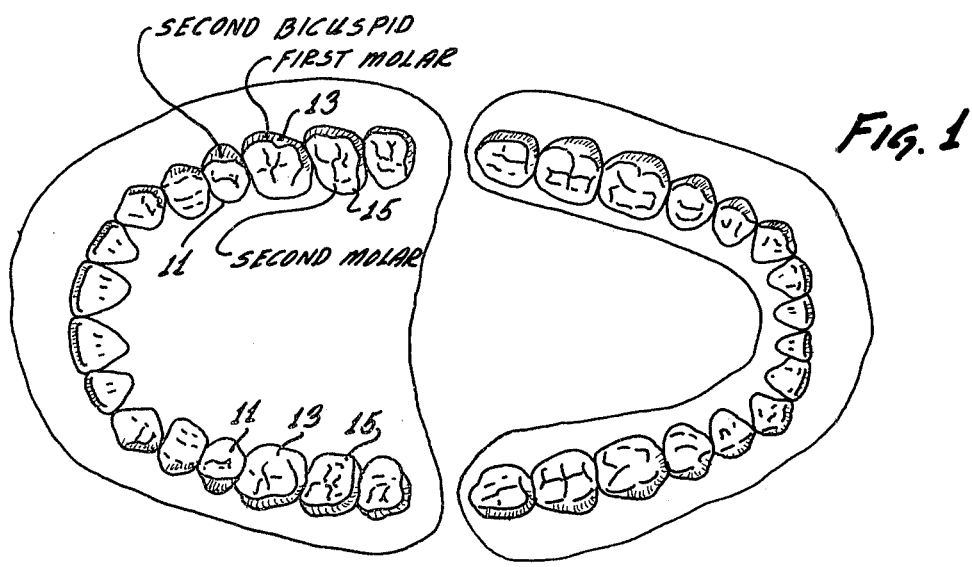
FIG. 1 is an occlusal view of a normal adult dental arch.

FIG. 1 shows the natural upper teeth of an adult including the second bicuspids 11, the first molars 13, and the second molars 15.

Figure 2:
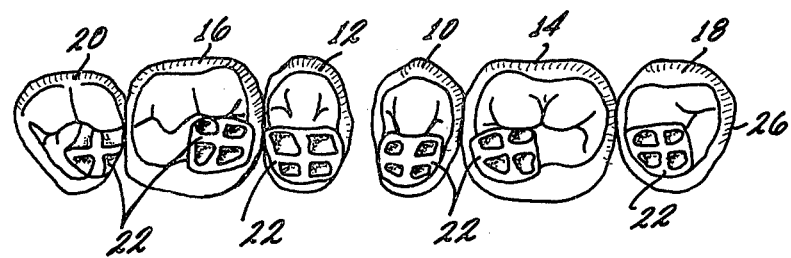
FIG. 2 is an occlusal view of artificial teeth constructed according to the present invention.
Figure 3:
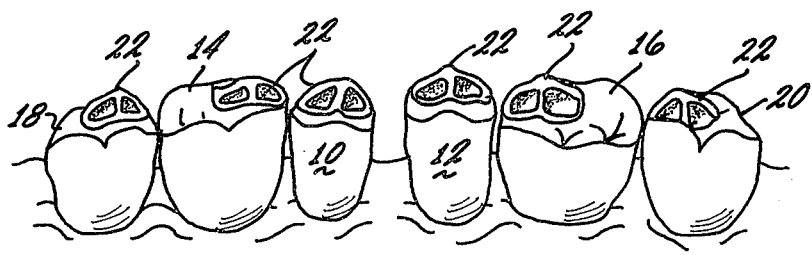
FIG. 3 is a perspective view of the teeth of FIG. 1 from the buccal side of the teeth.
Figure 4:
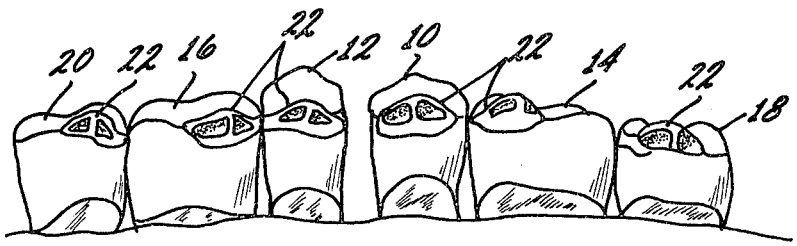
FIG. 4 is a lingual view of the teeth of FIG. 1.

Referring now to FIGS. 2, 3 and 4, wherein the same parts are indicated by like numbers, there are shown certain artificial upper teeth constructed according to the present invention. These include: upper left and right second bicuspid 10 and 12, upper left and right first molar 14 and 16, and upper left and right second molar 18 and 20.

From these figures it can readily be seen that a bladed insert 22 is always located on the lingual cusp of each tooth. Specifically, the bladed insert 22 conforms to the normal shape of the cusp that is replaced.

The upper teeth shown in FIGS. 2, 3 and 4 are opposed by lower plastic or acrylic teeth of conventional anatomic design.

As can be seen in FIGS. 5, 6 and 7 each of the bladed inserts 22 includes a head portion 40 including blades 42 and 44 which together form an arched cruciform structure conforming approximately to the envelope of a normal lingual cusp. This structure is quite strong mechanically and able to resist forces from any direction.

Blades 42 and 44 are not intended to be razor-sharp, but instead have a rounded edge. This design of the cutting blade represents a compromise between the very sharp blade, which creates a risk of damage to the lingual and buccal tissues and which is less strong and, at the other extreme, a very blunt blade which would be considerably less effective for cutting, shearing and shredding food. The bladed insert 22 further includes a post 46 to provide a means of anchoring the insert to an artificial tooth 26.

From FIGS. 5, 6 and 7 it can be seen that the shape of the insert 22 varies slightly depending on whether it is intended for use in a bicuspid, first molar, or second molar.

In the preferred embodiment, the insert 22 is attached to the tooth in the following manner. The precast bladed insert 22 is placed and held within an empty mold in which the artificial tooth is cast. This insures that the bladed insert 22 necessarily lies within the envelope of the artificial tooth. With the insert thus held in position, the acrylic resin in fluid form is introduced to the tooth mold, and upon curing, the resin adheres to the post 46 thereby securely anchoring the metal insert 22 to the artificial tooth. The artificial tooth thus produced may then be mounted into a denture in the usual manner.

Although the insert of the preferred embodiment is placed at the mesial lingual cusp of the molars, placement at the distal lingual cusp or at other cusps is also possible in other embodiments. Likewise, the use of one, two or three metal teeth is possible, depending on the wishes of the dentist and patient. The inserts can be placed in either upper or lower teeth.

In a preferred embodiment, the blade insert 22 is made of a chrome stainless steel. It would, of course, be obvious to use another material, particularly one whose color more nearly matches that of the artificial tooth.

Other means of attaching the bladed insert to the artificial tooth would be obvious to those skilled in the art. These include the use of a screw instead of post 46 of FIG. 4, or the use of cement or other adhesive to anchor the bladed insert to an artificial tooth.

The arched cruciform blade configuration of the tooth of the preferred embodiment has been found to be effective in practice because it is a strong structure. It has adequate sluicing, thereby preventing clogging by food. The effective area actually in contact with the food is small, greatly increasing the effective pressure exerted on the food. This in turn, permits a great improvement in the ability of edentulous patients to cut, shred and tear their food. Other blade configurations are conceivable, including a single blade and three intersecting blades.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. An insert for use as a lingual cusp of an anatomic artificial tooth, said insert comprising:
   means for cutting and shearing food including at least one blade having a convex edge arched outward away from the occlusal surface, said blade being formed of a substance harder than that of the artificial tooth; and
   means for securing the insert in the artificial tooth; whereby the user is able to chew and shear food with forces substantially less than those required by natural teeth, thereby permitting denture wearers to chew food without distress.

2. The insert of claim 1 wherein said means for cutting and shearing food further comprises a second blade having a convex edge arched outward away from the occlusal surface and intersecting the at least one blade to form a substantially cruciform shape.

3. The insert of the artificial tooth of claim 2 in which the insert's substantially cruciform shape approximately conforms to the envelope of at least one lingual cusp of an anatomical tooth.

4. The insert of the artificial tooth of claim 3 wherein said insert is of a chrome stainless steel.

5. The insert of the artificial tooth of claim 1 wherein said insert is of an abrasion-resistant, malleable material.

6. The insert of the artificial tooth of claim 1 wherein said tooth is a bicuspid.

7. The insert of the artificial tooth of claim 1 wherein said tooth is a first molar.

8. The insert of the artificial tooth of claim 1 wherein said tooth is a second molar.

9. The insert of claim 1 formed as a single piece of a durable malleable material.

10. The insert of claim 1 wherein said means for securing includes a post directed inward toward the occlusal surface for anchoring said insert to the tooth.

11. A unitary insert for an anatomical, artificial tooth, comprising:
   a substantially plate-like head portion of material harder than the artificial tooth having an upper face and a lower face, the surface area of said upper face being substantially equal to the area of a lingual cusp of the anatomical artificial tooth;
   a post portion extending downward from the lower face of said head portion and substantially perpendicular to it, for anchoring said insert to the artificial tooth, and,
   two cutting blades fromed from a substance harder than the artificial tooth, each extending upward from the upper face of said head portion in a convex arch conforming approximately to the envelope of a lingual cusp of the anatomical artificial tooth, said blades intersecting near their midpoints at substantially right angles to form an arched cruciform structure, adapted to allow a user of the tooth to chew and shear foods with forces substantially less than required with natural teeth so that denture wearers may chew foods without exerting painfully great pressures on the soft tissues of the gums.

* * * * *